United States Patent [19]
Falk

[11] Patent Number: 5,754,298
[45] Date of Patent: May 19, 1998

[54] METHOD AND APPARATUS FOR IMAGING SEMICONDUCTOR DEVICE PROPERTIES

[75] Inventor: Robert Aaron Falk, Renton, Wash.

[73] Assignee: OptoMetrix, Inc., Renton, Wash.

[21] Appl. No.: 711,420

[22] Filed: Sep. 5, 1996

[51] Int. Cl.$^6$ .................................................. G01N 21/00
[52] U.S. Cl. ............................ 356/390; 356/414; 356/343
[58] Field of Search ................................. 356/340, 414, 356/10, 343, 390

[56] References Cited

U.S. PATENT DOCUMENTS

| | | | |
|---|---|---|---|
| 4,758,092 | 7/1988 | Heinrich et al. | |
| 5,028,135 | 7/1991 | Cheung et al. | 356/340 |
| 5,280,272 | 1/1994 | Nagashima et al. | 356/340 |
| 5,540,494 | 7/1996 | Purvis, Jr. et al. | 356/340 |

OTHER PUBLICATIONS

Brunfeld, A. et al., "High Resolution Optical Profilometer," *SPIE*, 680:118–123, 1986.

Heinrich, H.K. et al., "Noninvasive Sheet Charge Density Probe for Integrated Silicon Devices," *Appl. Phys. Lett.*, 48(16):1066–1068, Apr. 1986.

Corle, T.R. et al., "Distance Measurements by Differential Confocal Optical Ranging," *Applied Optics*, 26(12):2416–2420, Jun. 15, 1987.

Falk, R.A. et al., "Optical Probe Techniques for Avalanching Photoconductors," *8th IEEE Pulsed Power Conference*, 29–32, 1991.

Schoenbach, K.H. et al., "Temporal Development of Electric Field Structures in Photoconductive GaAs Switches," *Appl. Phys. Lett.*, 63(15):2100–2102, 1993.

Chen, T. et al., "Measurement Principle and Error Analysis for an Optical Heterodyne Profilometer," *SPIE*, 2101:800–803, 1993.

Goldstein, M. et al., "Hetrodyn Interferometer for the Detection of Electric and Thermal Signals in Integrated Circuits Through the Substrate," *Rev. Sci. Instrum.*, 64(10):3009–3013, 1993.

Falk, R.A. et al., "Dynamic Optical Probing of High–Power Photoconductors," *9th IEEE Pulsed Power Conference*, pp. 88–91, 1993.

Falk, R.A. et al., "Electro–Optic Imagery of High–Voltage GaAs Photoconductive Switches," *IEEE Transactions on Electron Devices*, 42(1):43–49, 1995.

Adams, J.C., "Electro–Optic Imaging of Internal Fields in (111) GaAs Photoconductors," *IEEE Transactions on Electron Devices*, 42(6):1081–1085, 1995.

*Primary Examiner*—Frank G. Font
*Assistant Examiner*—Reginald A. Ratliff
*Attorney, Agent, or Firm*—Christensen O'Connor Johnson & Kindness PLLC

[57] ABSTRACT

A radiant energy point source (10) generates radiant energy, and a mechanism (12, 15, 16) focuses the radiant energy generated by the point source onto a target (18) and scans the target with the focused radiant energy. A collector (16, 14) collects the focused radiant energy that is scattered from the target and a splitter (22) splits the collected radiant energy into two paths. Each of the two paths of the collected radiant energy is focused onto separate focal spots by a focusing mechanism (24). A pair of spatial filters (26, 28) filter the collected radiant energy at the focal spots. The spatial filters are offset from each other along the path of the focused radiant energy. Detectors (30, 32) separately detect the focused radiant energy which passes through each of the spatial filters and produce signals proportional to the quantity of detected focused radiant energy present. Finally, the produced signals are combined into an image signal related to the distance traveled by the radiant energy from the focusing mechanism to the target and back to the collector.

15 Claims, 7 Drawing Sheets

METHOD AND APPARATUS FOR IMAGING SEMICONDUCTOR DEVICE PROPERTIES

This invention was made with Government support under Contract No. F29601-C-0096 awarded by the Department of the Air Force. The Government has certain rights in the invention.

FIELD OF THE INVENTION

This invention relates to methods and apparatus for imaging characteristics of a target, more specifically, methods and apparatus for accurately imaging internal characteristics of semiconductor circuits.

BACKGROUND OF THE INVENTION

Semiconductor Imagery

The internal characteristics of a semiconductor affect the optical properties, the optical absorption coefficient and the refractive index, within the semiconductor. Specifically, the internal characteristics of electric field, temperature, and carrier density cause changes in both optical properties. Absorption shifts are typically strongest at optical wavelengths near the semiconductor bandedge, whereas the refractive index shifts occur over a broad range of wavelengths. In Table 1, theoretical estimates for the magnitudes of the optical properties in terms of small signal variations for a gallium arsenide (GaAs) semiconductor and the effects of electric field (E) or hole density, temperature (T), and electron density ($N_e$) on refractive index (n) and absorption coefficient ($\alpha$), in GaAs are shown. Other semiconductor materials, such as silicon (Si) show similar results.

TABLE 1

| | Refractive Index | Absorption |
|---|---|---|
| Electric Field | $\frac{\delta n}{\delta E} = 3 \times 10^{-9}$ (cm/V) | $\frac{\delta \alpha}{\delta E} = 3 \times 10^{-3}$ (1/V) |
| Temperature | $\frac{\delta n}{\delta T} = 3 \times 10^{-4}$ (1/K) | $\frac{\delta \alpha}{\delta T} = 7$ (1/K*cm) |
| Carrier Density | $\frac{\delta n}{\delta E_c} = 4 \times 10^{-21}$ (cm$^3$) | $\frac{\delta \alpha}{\delta E_c} = 3 \times 10^{-19}$ (cm$^2$) |

Absorption imagery in GaAs has been described by Schoenbach et al., "Temporal Development of Electric Field Structures in Photoconductive GaAs Switches," Appl. Phys. Lett. 63, 2100-2 (1993), and Falk et al., "Dynamic Optical Probing of High-Power Photoconductors," 9th IEEE Pulsed Power Conference, 88-91 (1993). In general, a wavelength near the material bandedge is utilized to illuminate the sample of interest and an image of the sample is obtained on an appropriate detector, e.g., a charged coupled device (CCD) camera. These techniques perform adequately for large changes in absorption, but have limited sensitivity when compared to interferometric techniques. Further, calibration for absorption imagery can prove difficult due to the rapid changes in absorption with changes in the internal properties, as described in "Optical Probe Techniques for Avalanching Photoconductors," Eighth IEEE International Pulsed Power Conference, by R.A. Falk et al., 29-32 (1991).

Electric fields only affect the refractive index of semiconductors which are noncentrosymmetric. For example, strong electro-optic effects occur in GaAs but not in Si. Techniques for obtaining electro-optic images in noncentrosymmetric semiconductors, specifically GaAs, are described by R.A. Falk et al. in "Electro-Optic Imagery of High-Voltage GaAs Photoconductive Switches," IEEE Trans. Electron Devices 42, 43-9 (1995) and by J.C. Adams et al., "Electro-Optic Imaging of Internal Fields in (111) GaAs Photoconductors," IEEE Trans. Elect. Devices 42, 1081-85, (1995). These techniques involve analyzing the polarization rotation of light passing through a GaAs sample, wherein the optical wavelength is well below the absorption bandedge of the GaAs sample. In order to compensate for the multi-valued nature of the polarization rotation, specialized algorithms were utilized for processing the images. Although a remarkable measurement, the techniques employed fail to work in semiconductors such as Si and are only useful for electric fields, i.e., they are not applicable to temperature or carrier density measurements.

Heinrich et al. and Goldstein et al. have demonstrated optical, high-speed sampling of carrier density and thermal effects in semiconductors at a single spatial point. They reveal that electric field could be sensed indirectly through the change in carrier density which occurs in the depletion region of reversed biased junctions. The work of Heinrich et al. is described in "Noninvasive Sheet Charge Density Probe for Integrated Silicon Devices," Appl. Phys. Lett. 48, 1066-8, (1986). The work of Goldstein et al. is described in "Heterodyne Interferometer for the Detection of Electric and Thermal Signals in Integrated Circuits through the Substrate," Rev. Sci. Instrum. 64, 3009-13 (1993). Both groups utilize interferometric means to extract a signal from the changes in refractive index caused by the two optical effects. In both cases, a pair of optical beams is brought through the back side of the semiconductor device. One beam, used as a reference, is reflected off a convenient point on the upper surface of the device and brought back into an optical detector. The second beam is positioned onto the point of interest, reflected off of the upper surface and combined with the reference beam to form the interferometric signal. In the case of Heinrich et al., a modified Nomarski interference microscope was utilized as the interferometric system. Goldstein et al. utilized a variant on a heterodyne, interference microscope.

The detection schemes of Heinrich et al. and Goldstein et al. were performed at a single point. A seemingly obvious extension of their work would be to scan the optical beam(s) in order to assemble an image of the target. However, this presumption proves false in the face of actual semiconductor devices. In both techniques, the detected light returns to the optical system after reflection from either the metalization or the refractive index changes at the upper surface of the semiconductor. Reflections from the back surface are assumed to be rejected by the optical system. In a typical semiconductor, the optical path length to the reflective interface is not constant with position. Path length differs due to changes in the physical height of the upper surface and the refractive index of intervening layers. The optical path length variations are of the order of the optical probe wavelength in the semiconductor, i.e., large compared to the expected signals. In addition, large changes in the reflection coefficient occur as the optical probe is moved around the upper surface. Thus, unlike the previous single point detection methods, imaging requires the sensing of a small phase signal on top of large phase background phase signals and reflection amplitude variations.

The method of Heinrich et al. is particularly ill suited to deal with these issues. Heinrich et al. requires the use of a convenient reference spot. As described, the reference spot is at a fixed distance from the probe and it is clear that not all points on the device are convenient. More specifically, as the beams are scanned, the relative phase and amplitude between the two optical beams will shift. The phase shifts bring about difficulty in maintaining optimal signal-to-noise condition. In fact, a relative phase shift of π/2 can cause the small signal response to be zero. Amplitude shifts cause degradation in the signal-to-noise due to reduced fringe contrast. The temporal variations in amplitude and phase shifts resulting from the scanning process can also produce false signals. Even if means to scan the probe beam while fixing the position of the reference beam were introduced, these defects would still be present. Heinrich et al. neither discuss the option of imaging nor describe means of overcoming the above difficulties.

Goldstein et al. utilize heterodyne techniques, which convert the DC signals of Heinrich et al. into an AC signal at the heterodyne frequency. At first glance, the heterodyne methodology would appear to remove several of the above objectionable defects. However, the "spectral analysis" given by Goldstein et al. obscures several points and in one case yields incorrect conclusions. An analysis of a heterodyne interferometer, which uses the standard starting points of time varying amplitude and phase, is given in Chen et al. "Measurement Principle and Error Analysis for an Optical Heterodyne Profilometer," T. Chen, Z. Li, J.B. Chen, Proc. SPIE 2101, 800-3 (1993). The Chen analysis clearly shows that the heterodyne signal is subject to the same defects as the Heinrich approach. However, as this point is rather important, the equations relating to phase detection in Goldstein et al. will be reviewed in some detail.

It is first noted that the reference field (second equation in Equation 3 of Goldstein et al.) and the probe field (Equation 7 of Goldstein et al.) are given the same time dependent amplitude coefficient, A(t). An independent term describing relative amplitude variations in the two fields is not included. The conclusion in Goldstein et al., that the final phase signal shown in their Equation 10 is independent of amplitude modulations, is therefore incorrect. Their Equation 10 contains no amplitude modulations simply because none were included in the starting fields. Allowing for independent variations in the amplitudes, A(t), clearly introduces amplitude noise into Equation 10. Chen et al. shows the correct dependence on relative amplitudes and their effect on fringe contrast, etc.

The second point about the Goldstein et al. analysis is somewhat more subtle due to the "spectral analysis" approach used. In their analysis, they assume that the signal is given by a single frequency phase modulation along with a fixed relative phase angle, Φ. General time dependencies are presumably analyzed by Fourier decomposition. Equation 10 therefore indicates that Φ is an unimportant additive phase, which can presumably be removed by AC coupling techniques. If Φ is not assumed to be constant, however, this is no longer the case. The spectral components of the Φ term will mix with the single frequency term in the cosine creating numerous sidebands and amplitude dependencies. The exact effect depends on the amplitudes of various frequency components and appears complex in the Goldstein et al. analysis. The Chen et al. analysis avoids the "spectral analysis" approach and clearly shows that the two phase effects (phase signal and background variations) contribute equally to the final signal.

Both the Heinrich et al. and Goldstein et al. techniques suffer reduced transverse resolution due to defocusing, which occurs as the beam is scanned over an uneven surface. Additionally, optical returns from intervening layers and objects (e.g. defects) can cause signal degradation in the Heinrich et al. technique. The Goldstein et al. technique may be able to reject out of focus returns. However, this conclusion depends upon details of the optical system which are not given.

Scanning Confocal Imagery

Scanning confocal imagery differs from standard imaging systems in that individual image pixels are gathered sequentially, one at a time, from a spot focused onto the object being imaged. The main disadvantages of this system are the inability to capture images of single-shot events and the need for either a mechanical or optical scanning system. The former is fundamental, where as the latter simply adds system complexity in some areas while potentially decreasing it in others. The advantages of the scanning system are numerous and include: 1) extended wavelength range while maintaining high detection efficiency, 2) improved transverse resolution, 3) improved depth discrimination, 4) extended field of view, and 5) extended on-line processing.

Confocal systems come in two arrangements Type 1 and Type 2 (for details of confocal systems, see *Confocal Microscopy*, T. Wilson, Ed., Academic Press (1990)). The distinction between the two types is that the Type 2 system focuses the light returned from the target through a pinhole prior to detection. Although a seemingly small difference, the inclusion of the pinhole causes profound differences in the optical performance of the two types of systems. Of specific interest herein is the difference in optical response with target distance.

Assume that the target is moved back and forth along the optical axis. For small changes in the target position the detector in the Type 1 system will record no variation in optical intensity. This result derives from the detector being underfilled. For large variations in the target position, the detector will eventually become overfilled. At this point, a relatively slow $1/z^2$ variation in the optical intensity will occur, where z is the target displacement from the focused position. Brunfeld et al., "High Resolution Optical Profilometer," SPIE 680, 118-23 (1986), have used this effect to produce a depth of focus sensor with resolution on the order of a tenth micron.

Variation in the optical intensity with longitudinal displacement of the target is quite different for the Type 2 confocal system. The coherent nature of the Type 2 system yields a response of the form $$I(\alpha) = I_0 \left[ \frac{\sin(\alpha)}{\alpha} \right]^2 \text{ with } \alpha = u/2 = \frac{8\pi}{\lambda} \left( \frac{a}{2f} \right)^2 z \quad (1)$$

where $I_0$ is the peak optical response, α is defined as the modified optical coordinate, μ is the standardly defined optical coordinate, λ is the optical wavelength, α is the lens diameter, $f$ is the collection lens focal length and z is the longitudinal target displacement from the lens focal spot. The squared part of the equation after the $I_0$ term is defined as the longitudinal transfer function of the system. This functionality falls off much faster than for the Type 1 system. For typical values of the variables, the intensity will fall off to half the peak value in less than 1 micrometer of target displacement.

It is important to note that the symmetry of the optical system does not distinguish between where in the optical path from the target and the point detector (pinhole-photodetector combination) that the optical path length, z, varies. Specifically, changes in the point detector position or in the refractive index along the optical path produce equivalent results to changing the target position.

The strong intensity variation with target distance in a Type 2 confocal system has been used for years to obtain rough distance information and to produce 3-D images (*Confocal Microscopy*, T. Wilson, Ed., Academic Press (1990)). T.R. Corle et al. "Distance Measurements by Differential Confocal Optical Ranging," Applied Optics 26, 2416-20 (1987), were able to obtain interferometric accuracies and resolutions by using a technique that produced a signal proportional to the derivative of the intensity response in Equation 1 above. In their system, the target was vibrated at frequency, ω, which results in a signal at that frequency which is proportional to the derivative. The main zero crossing of this derivative occurs at the peak response of the system and can be used to accurately determine the target distance. Resolution better than 0.01 nanometer was demonstrated. There exist several difficulties with this technique: 1) it is often impractical to vibrate the target of interest; 2) temporal sampling resolution is limited by the vibration frequency; 3) the system is open loop and if made closed loop, the loop closing time would be limited by the vibration frequency; 4) varying optical intensity can produce signal errors; and 5) ultra-high speed optical pulse sampling techniques, such as used by Heinrich et al. would prove difficult.

The present invention is directed to overcoming the foregoing and other disadvantages. More specifically, the present invention is directed to providing a method and apparatus suitable for confocal imaging internal characteristics of a target, such as the internal characterisics of semiconductor circuits.

SUMMARY OF THE INVENTION

In accordance with this invention, a method and apparatus for confocal imaging internal characteristics of a target, such as semiconductor circuits, is provided. An imaging system in accordance with this invention includes a radiant energy point source for generating radiant energy, and a mechanism for focusing the radiant energy generated by the point source onto a target and scanning the target with the focused radiant energy. The system also includes a collector for collecting the focused radiant energy that is scattered from the target and a splitter for splitting the collected radiant energy into two paths. Each of the two paths of the collected radiant energy is focused onto separate focal spots by a focusing mechanism. A pair of spatial filters are provided for filtering the collected radiant energy, one spatial filter for each of the two paths of the collected radiant energy. Each of the spatial filters is placed approximately at one of the focal spots. The spatial filters are offset from each other along the path of the focused radiant energy. The system further includes detectors for separately detecting the focused radiant energy that passes through each of the spatial filters and produces signals proportional to the quantity of detected focused radiant energy present. Finally, the system includes a mechanism for combining the produced signals into an image signal related to the distance traveled by the radiant energy from the focusing mechanism to the target and back to the collector.

In accordance with other aspects of this invention, the radiant energy is optical radiation.

In accordance with further aspects of this invention, the focusing mechanism includes a first lens for collimating the optical radiation, and a second lens for focusing the collimated optical radiation onto the target. The collector includes the second lens for collimating the scattered optical radiation from the target along the optical path to the first lens, and a beam splitter for redirecting the optical radiation to the splitter, wherein the splitter is a Wollastan prism. The focusing mechanism is a third lens, the spatial filters are pinholes, wherein the offset of the pinholes is mechanically set to a predetermined value, and the detectors are a pair of photodetectors. The system further includes an electronic circuit for producing an image signal, wherein the image signal is the difference in the signals generated by the pair of photodetectors divided by the sum of the signals generated by the pair of photodetectors. The image signal is produced according to the optical path length between the second lens and the target with the exact nature of the relationship being determined by the particular values of the pinhole offsets and the image signal being independent of the return optical intensity.

In accordance with still other aspects of this invention, the imaging system further includes a controller for electronically controlling the spatial filter offsets, wherein the controller includes an electro-optic substrate placed between the third lens and the two pinholes. The electro-optic substrate has a transparent electrode on one side which is common to both optical paths and a pair of transparent electrodes on the opposing side with each of the pair arranged to intersect only one of the pair of optical paths produced by the combination of the Wollastan prism and the third lens. Application of a voltage to one of the pair of transparent electrodes and the common electrode changes the refractive index of the part of the electro-optic substrate which intersects, changing one of the pair of optical paths and thereby adjusting the image signal.

In accordance with still further aspects of this invention, an electronic feedback circuit changes the common pinhole offset according to changes in the optical path length between the second lens and the target. The electronic feedback circuit further includes a feedback amplifier which applies a common voltage between the pair of transparent electrodes and the common transparent electrode of the electro-optic substrate for maintaining a constant value of the image signal with the applied common voltage becoming a new image signal, thereby obtaining a closed loop system, wherein signal linearity is determined by the linearity of the electro-optic substrate and the closed loop system is able to track changes in the optical path length between the second lens and the target.

In accordance with still yet other aspects of this invention, the imaging system further includes a changing mechanism for changing the intensity of the optical radiation point source to maintain a constant total intensity at the pair of photodetectors. The changing mechanism further includes a feedback amplifier which has as an input a signal proportional to the sum of the intensities at the pair of photodetectors and applies a signal to a light source whose intensity is proportional to the signal so as to maintain a constant value of the sum of the outputs from the photodetectors, thereby allowing maintenance of a signal-to-noise ratio in the image signal which is independent of the targets optical characteristics.

As will be readily appreciated form the foregoing summary, the invention provides a new and improved method and apparatus for imaging internal characteristics of a target, such as the internal characterisics of semiconductor circuits.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
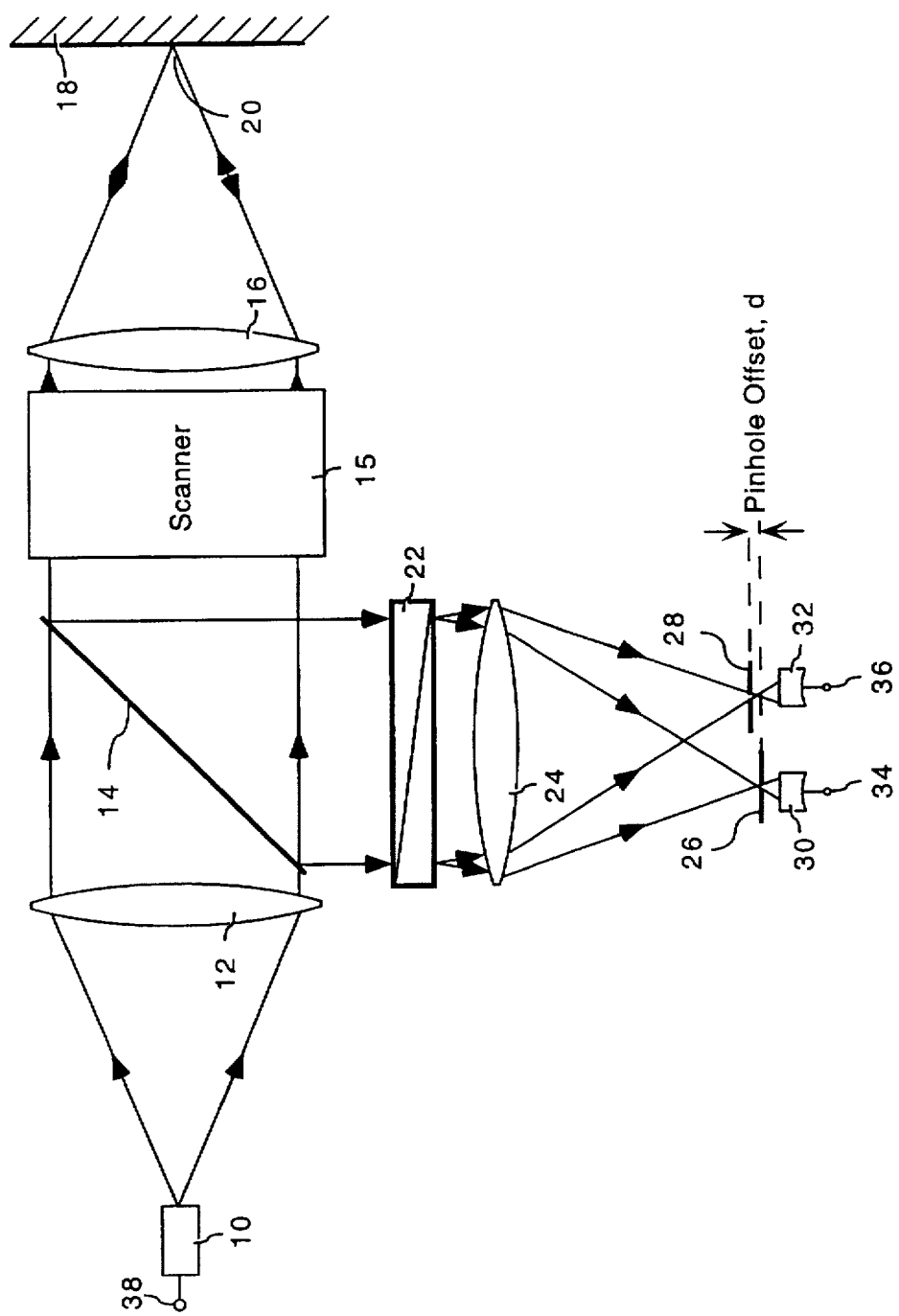
FIG. 1 is a schematic diagram of a dual detector confocal imaging system.

FIG. 1 sets forth a preferred embodiment of an optical system for imaging small refractive index changes in accordance with the present invention, specifically as applied to imaging refractive index changes which occur in semiconductor devices due to electric field, temperature, carrier density, and other properties.

The imaging system includes an illumination portion and a light collection and detection portion. The illumination portion includes a point light source 10, such as a laser focused through a pinhole, a first lens 12 which collimates light from the point source, a beam splitter 14 and a second lens 16 which focuses collimated light on a focal spot or point 20 on a target 18. Between beam splitter 14 and second lens 16 is a scanner 15 which can be any one of a number of optical scanners typically used in confocal imagery, such as mechanical scanners, acousto-optic scanners and mechanical target motion scanners. The light collection and detection portion includes a target 18 which reflects focused light from second lens 16, with the second lens 16 and the beam splitter 14 as common elements with the illumination portion. In addition, the light collection and detection portion includes a Wollastan prism 22 or equivalent device for splitting an optical beam into two parts, a third lens 24, a first pinhole 26, a second pinhole 28, a first detector 30 with a first detector output 34 and a second detector 32 with a second detector output 36. Finally, an intensity control 38 modulates the optical intensity of point light source 10. Point light source modulation can take on many forms depending on the nature of the optical source. For example, an external electro-optic or acousto-optic modulator might be employed. Alternatively, the current applied to an optical source such as a laser diode or light emitting diode may supply the modulator.

Operation of Invention

The imaging system shown in FIG. 1 is a modified confocal imaging system. The configuration shown in FIGS. 1 and 3 and described below is one example of an implementation of the confocal imaging system of the present invention. Other implementations, e.g. acoustic, electron-beam, can also effectively operate within the confocal imaging system of the present invention. The configuration shown performs reflection imagery.

The optical paths in the system are indicated by the lines with arrows, a pair of lines indicating an optical beam between components of the system. The arrows indicate the direction of the optical beam in each section of the system. As shown in FIG. 1, light emerging from point light source 10 is collimated by first lens 12 and passes through beam splitter 14 and scanner 15 to second lens 16. Some light losses are expected at beam splitter 14. The use of suitable polarization optics minimizes light losses for polarized light. Second lens 16 focuses the light of point light source 10 onto target 18 at focal spot 20. Scanner 15 scans the focal spot transversely over the target. Conversely the optical light beam can remain stationary and the target moved transversely to scan the section of interest. Confocal imagery utilizes the scanning process to produce an image of the target. For best operation of the confocal system, focal spot 20 is diffraction limited. Generally, diffraction limited operation requires that first lens 12 and second lens 16 are corrected for aberrations, such as spherical aberration. These corrections imply the use of compound lenses. In addition, the physical size of point light source 10 must be less than the diffraction limit of first lens 12. Relaxation of the diffraction limit requirement reduces the sensitivity of the system and the transverse resolution of the images. This reduction is acceptable for certain operations.

The light beam reflected from target 18 is collected by second lens 16 and recollimated. Beam splitter 14 receives the reflected collimated light beam from second lens 16 and reflects the light beam received from second lens 16 to the Wollastan prism 22. The Wollastan prism 22 receives the reflected light beam from the beam splitter 14 and divides the reflected light beam into two divergent light beams. Beam splitters with properties similar to the Wollastan prism may be used in its place. The angle separation of the divided light beams is small enough to allow a single lens 24 to process them. The separation angle between the two output optical beams is determined by the type of the Wollastan prism 22.

The two sets of two angularly separated beams produced by the Wollastan prism 22 pass through third lens 24. The third lens 24 focuses a first beam from the set of separated beams at a first pinhole 26. Also, the third lens 24 focuses a second beam from the set of separated beams at a second pin hole 28. The third lens causes the angular separation of the beams produced by the Wollastan prism 22 to produce a pair of focal spots separated transversely by a distance given by (for small angles) the product of the separation angle in radians and the focal length of the third lens. The first beam passes through pinhole 26 and is received by first detector 30 and the second beam passes through pinhole 28 and is received by second detector 32. First detector 30 and second detector 32 convert the light beams falling upon them into electrical output signals indicated by first detector output 34 and second detector output 36. Optical detectors such as PIN diodes and photomultiplier tubes that exhibit a linear relationship between the optical intensity at each detector and the electrical output can be used for detectors 30 and 32. Diffraction limited operation is also desirable in this part of the optical system. Requirements are placed on the quality of third lens 24 and the size of pinholes 26 and 28 to be smaller than the diffraction spot size of the third lens 24, as described above.

As shown in FIG. 1, first pinhole 26 and second pinhole 28 are offset along the optical path, i.e., longitudinally, from the focal spots produced by third lens 24 processing of the beams output from the Wollastan prism 22. For purposes of this discussion, each pinhole is assumed to be offset by an equal amount from each focal spot, one towards the third lens 24 and one away from the third lens 24. As shown, first pinhole 26 is placed away from the third lens 24 and second pinhole 28 is placed towards the third lens 24. The total longitudinal offset between the pinholes is the pinhole offset, d.

In order to understand the operation of the current invention, target displacement z in Equation (1) above is equivalent to pinhole displacement, for small displacements. In a confocal imaging system these two displacements are mathematically equivalent within a multiplicative factor. The multiplicative factor for the optical arrangement in FIG. 1 is the ratio of the second lens focal length over the third lens focal length. That is to say, a longitudinal movement of the target 18 is equivalent to a longitudinal movement of the pinholes 26 and 28.

The output signal at first detector output 34 is indicated by the quantity "a" and the signal at second detector output 36 is indicated by the quantity "b". Both signals are proportional to the optical intensity given in Equation (1). For the moment it is assumed that the proportionality is the same for quantities "a" and "b". The proportionality of quantity "a" and "b" are described in more detail below. If the quantities "a" and "b" are summed, a summed signal that is proportional to the optical source intensity, target reflectance and optical system losses is obtained. Quantity "a" minus quantity "b" yields a differenced signal that has all the previous proportionaities with the addition of representing a finite difference approximation to the derivative of the longitudinal transfer function given in Equation (1). Taking the ratio of the differenced signal over the summed signal removes the dependencies on the system variables, e.g., optical source intensity, leaves only the longitudinal dependency and produces a ratio signal. The ratio signal, r, is given by $$r = \frac{I(\alpha + d/2) - I(\alpha - d/2)}{I(\alpha + d/2) + I(\alpha - d/2)} = \frac{I(\alpha' + d') - I(\alpha')}{I(\alpha' + d') + I(\alpha')} \quad (2)$$

$$\text{with } d' \equiv \frac{8\pi}{\lambda} \frac{f_2}{f_3} \left(\frac{a}{2f_2}\right)^2 d \text{ and } \alpha' \equiv \alpha - d/2 \quad (3)$$

where α was defined in Equation (1). $f_2$ is the focal length of the second lens 16 and $f_3$ is the focal length of the third lens 24.

Figure 2:
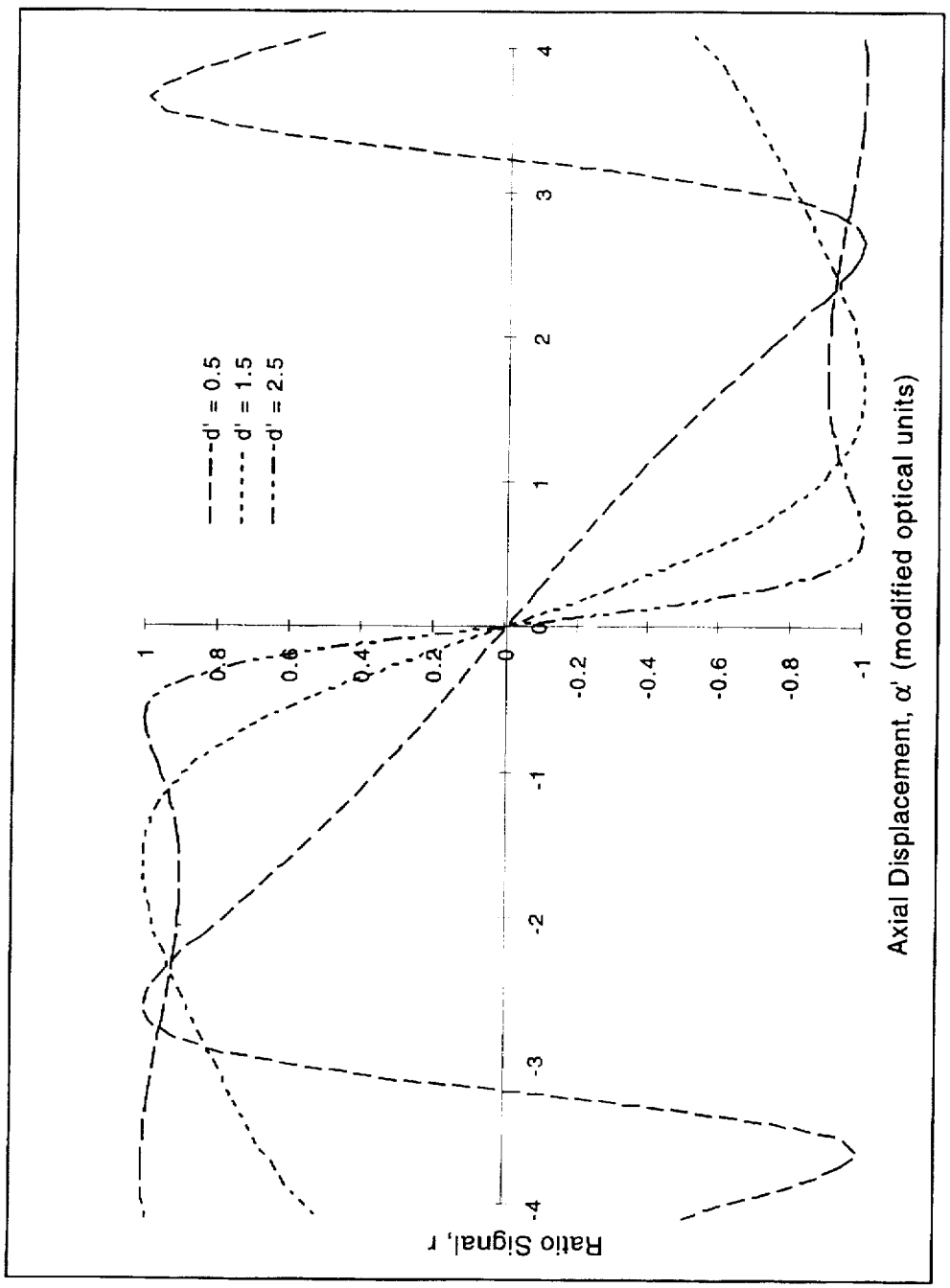
FIG. 2 is a graph of various signal response curves of the system of FIG. 1.

Referring to FIG. 2, values of r versus α' are shown for several values of offset d'. The ratio signals all pass through zero at zero displacement, have odd symmetry, and have an approximately linear region surrounding zero displacement followed by a peak and oscillatory behavior at large displacement. The slope of the linear region depends on the offset d'. The curve of r versus α' is the optical transfer function of the current invention.

The ratio signal r can be used to directly produce an image whose intensity values are proportional to the target displacement for displacements within the linear region. Displacements outside the linear regime produce an image whose intensity is multivalued with target displacement and an image of dubious value. Changing the pinhole offset d allows the sensitivity to be varied. High sensitivities are achieved by choosing larger pinhole offsets. However, this increase is at the expense of a narrower range of operation. Offsets d' larger than π are in general not useful due to the multivalue nature of the differential transfer function for such large offsets. This operation is referred to as open loop operation of the optical system. The electronic system for obtaining the ratio signal r is described in detail below with FIG. 4.

Figure 3:
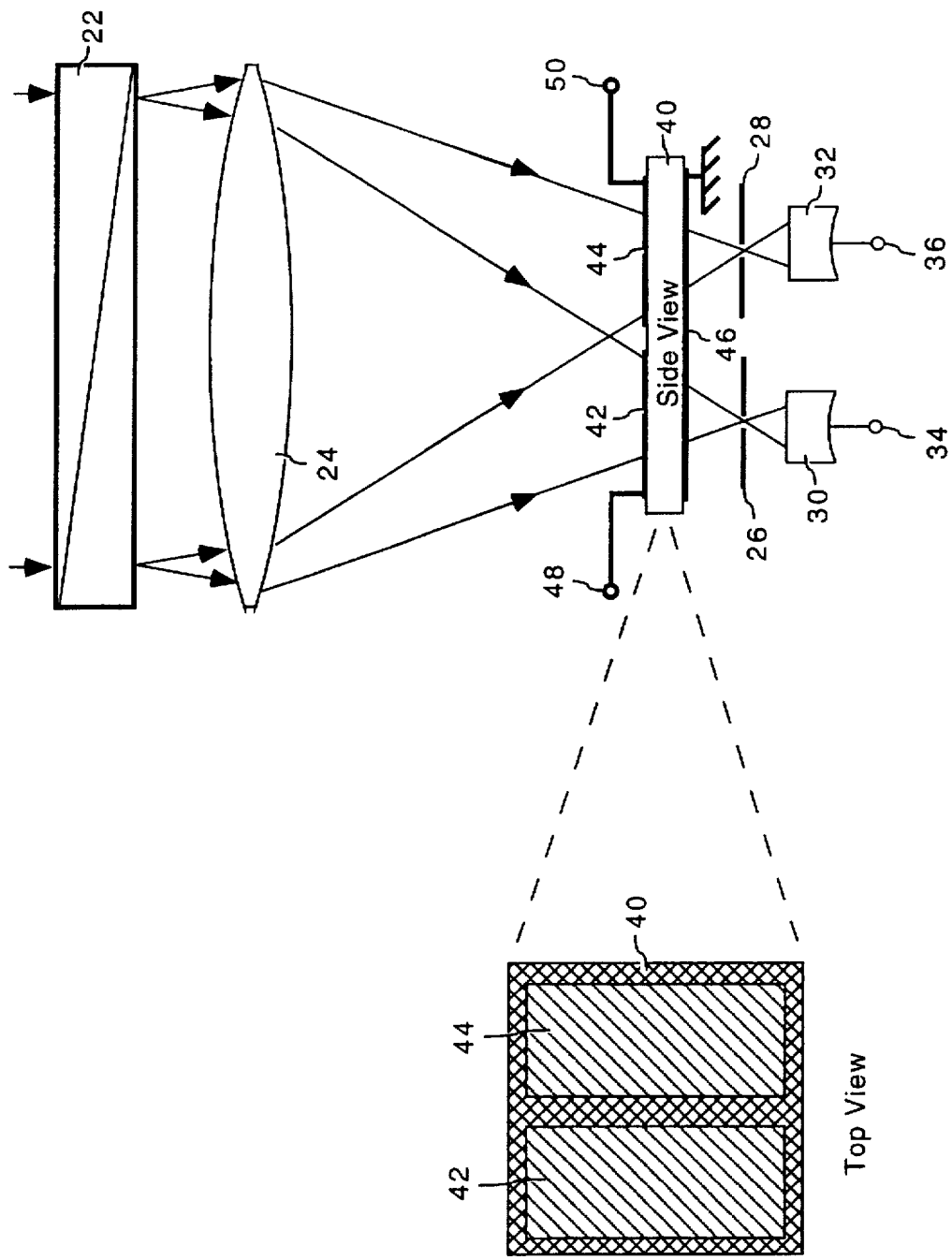
FIG. 3 is a shematic diagram of the dual detector confocal imaging system of FIG. 1 with an electro-optic substrate.

As can be seen from the above discussion, it is desirable to maintain the ratio signal r within the linear region surrounding zero displacement. The ability to rapidly adjust the pinhole offset d is also a desirable function. FIG. 3 shows the preferred embodiment for obtaining these desired functions. FIG. 3 includes the elements of the optical system in FIG. 1 and a device for electronically controlling the pinhole offset and path length from third lens 24 to the first and second pinholes 26 and 28. As described above, varying these parameters is equivalent (within a multiplicative factor) to varying the distance between target 18 and second lens 16. The desired variation could be accomplished by physically moving the first and second pinholes 26 and 28. However, physical movement can be slow and would typically require sub-micrometer positioning accuracy.

Figure 4:
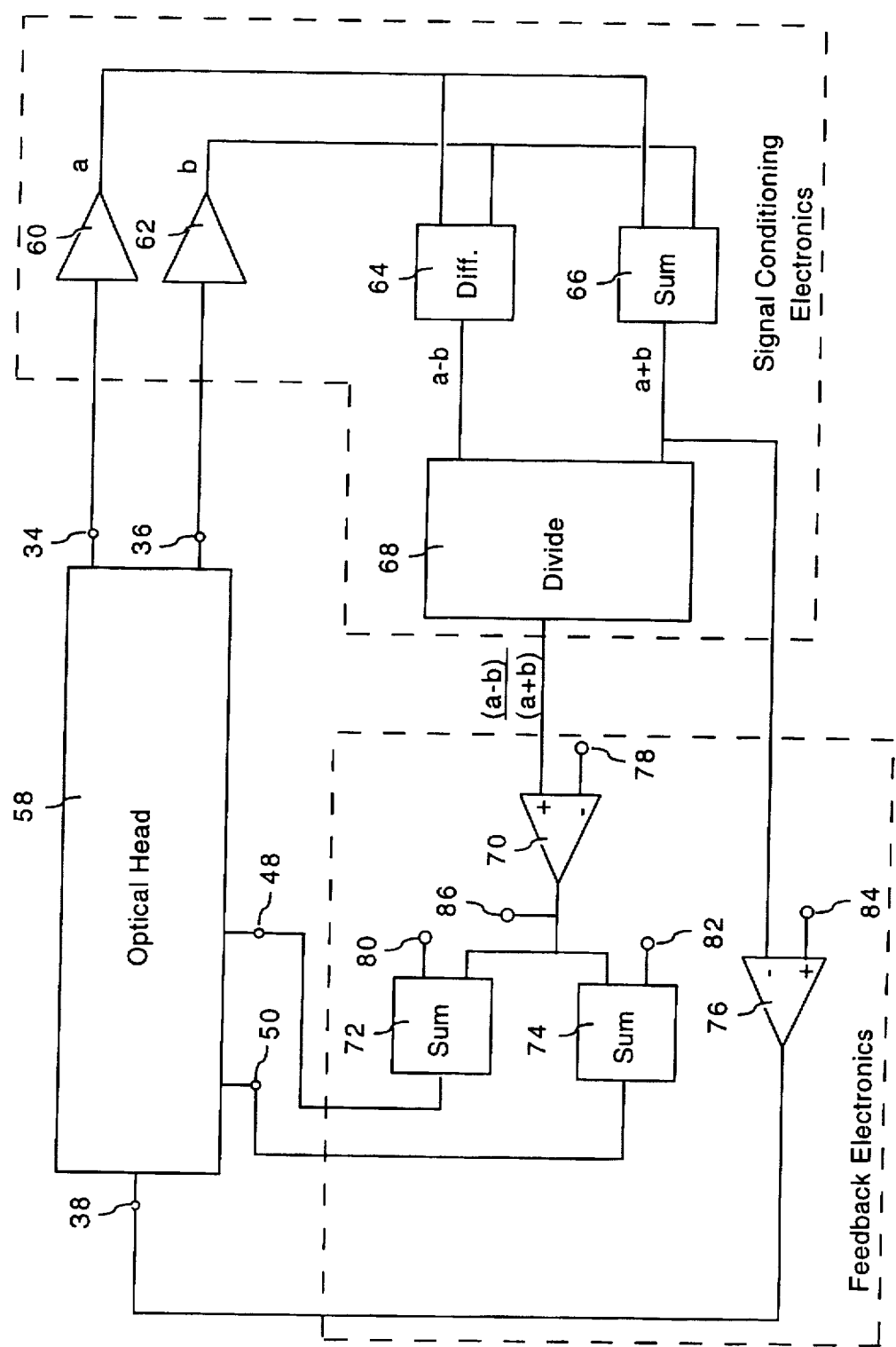
FIG. 4 is a functional block diagram of the dual detector confocal imaging system of FIG. 3 with an electronic feedback control circuit.

The preferred methodology for varying the optical path length between third lens 24 and the first and second pinholes 26 and 28 is performed by placing electrooptic substrate 40 in combination with first differential electrode 42, second differential electrode 44 and common electrode 46 between the third lens 24 and the pair of pinholes 26 and 28. The electro-optic substrate 40 is fabricated from a material, such as lithium tantalate, whose refractive index varies linearly with applied electric field. A voltage to first electrode connection 48 produces an electric field in electro-optic substrate 40 between first differential electrode 42 and the grounded common electrode 46. The resultant electric field produces a change in the refractive index of the substrate in the area covered by first differential electrode 42, which in turn changes the optical path length between third lens 24 and first pinhole 26. Similarly, a voltage applied to second electrode connection 50 changes the optical path length between third lens 24 and second pinhole 28. If a common voltage is simultaneously applied to first electrode connection 48 and second electrode connection 50, the common optical path length is changed. If a differential voltage is applied to first electrode connection 48 and second electrode connection 50, the pinhole offset d is changed. Thus, applying common and differential voltages to the electrode connections 48 and 50 allows electrical control of the position and offset of the first and second pinholes 26 and 28. The physical longitudinal offset of the first and second pinholes 26 and 28 can be any convenient value. In FIG. 4 the physical longitudinal offset is set at zero.

Also, note that according to optical equivalency described above, the common optical path length can also be changed by varying the optical distance between target 18 and second lens 16. Varying the optical distance between target 18 and second lens 16 can be obtained by physical movement of the target 18 or electro-optic techniques.

Electronically adjusting the common and differential optical path lengths between third lens 24 and first pinhole 26 and between third lens 24 and second pinhole 28 allows for closed loop operation of the optical system. In general, closed loop operation of a sensor yields better results than open loop operation. FIG. 4 shows electronic components for producing an open loop signal and components for producing a closed loop signal. As shown in FIG. 4, the optical imaging system, in FIGS. 1 and 3, is reduced to a single functional block, optical head 58. The optical head 58 includes five leads: first detector output 34, second detector output 36, intensity control 38, first electrode connection 48 and second electrode connection 50.

The electronic circuitry of the present invention includes signal conditioning electronics 56 and feedback electronics 59. The signal conditioning electronics 56 include first amplifier 60 and second amplifier 62 with inputs from first detector output 34 and second detector output 36, respectively. The relative gains of the first and second amplifiers 60 and 62 are adjusted to compensate for any differences in the optical response of the first and second detectors 34 and 36.

The outputs of the first and second amplifiers, "a" and "b," are input into difference circuit 64, which produces signal "a−b," and into sum circuit 66, which produces signal "a+b." The signals "a−b" and "a+b" are sent to the divide circuit 68, which produces signal "(a−b)/(a+b)." This last signal is the ratio signal r, see Equation (2). Signal "a+b" is a first output and signal "(a−b)/(a+b)" is a second output of the signal conditioning electronics 56. The signal conditioning electronics 56 produces open loop operation.

Closed loop operation is achieved by the feedback electronics 59. The feedback electronics 59 include first operational amplifier 70, second operational amplifier 76, a second sum circuit 72 and third sum circuit 74. The signal "a−b)/A+b)" from the divide circuit 68 is applied to the non-inverting input of the first operational amplifier 70. The inverting input of the first operational amplifier 70 is a first bias input 78. The first bias input 78 would typically be set to zero. When the feedback loop is closed, the value of the first bias input 78 causes the output of the divide circuit 68 to be driven to zero, as described below. The output of first operational amplifier 70 is called the range image output 86 and is input to the second sum circuit 72 and third sum circuit 74. Second sum circuit 72 has an additional input, first offset input 80, and third sum circuit 74 has an additional input, second offset input 82. The output of the second sum circuit 72 is connected to first electrode connection 48, therefore causing a positive output from the second sum circuit 72 to increase the optical path length between third lens 24 and first pinhole 26, see FIG. 3. The output of the third sum circuit 74 is connected to second electrode connection 50, therefore causing a positive output from the third sum circuit to increase the optical path length between third lens 24 and second pinhole 28, see FIG. 3. Negative output from either the second or third sum circuits 72 and 74 decreases the optical path lengths. The feedback loop is now closed.

Assume that the first offset input 80 is set to value V, second offset input 82 is set to −V and the output of first operational amplifier 70 is zero. The outputs of second sum circuit 72 and third sum circuit 74 are then V and −V, respectively. As described above, the application of these voltages to first electrode connection 48 and second electrode connection 50, respectively, will cause an effective displacement, d, between the first and second pinholes 26 and 28. A non-zero output from first operational amplifier 70 is applied equally to both first electrode connection 48 and second electrode connection 50, thus affecting the optical path lengths between the third lens 24 and the first and second pinholes 26 and 28.

The following illustrates the effect of feedback electronics. Assume that the pinhole offset is set to some non-zero value, d, and that the output of the divide circuit 68 is initially positive, representing a negative displacement of the target within the linear region of the transfer function. Further assume that first bias input 78 is set to zero. As a consequence, the output from the first operational amplifier 70 is a positive signal. The positive signal is applied to both the first and second electrode connections 48 and 50, which increases both optical path lengths between the third lens 24 and the first and second pinholes 26 and 28. As described above, an increase in pinhole distance from third lens 24 is equivalent to an increase in the target distance from the second lens 16. As shown in FIG. 2, the optical transfer function indicates that an increase in target distance decreases the value of r, therefore the output of the divide circuit 68 is reduced toward zero. Through an equivalent argument, an initially negative output from the divide circuit 68 is also driven toward zero. Thus, the closed loop drives the output of the divide circuit 68 to zero, or more precisely, to the input value at first bias input 78. The closed loop arrangement allows tracking of the optical path length between the second lens 16 and the target 18. This tracking can occur over path length differences that exceed the size of the linear region of the transfer function shown in FIG. 2, as long as the change in path length is slower than loop convergence time.

Proper time convergence of the loop depends on the gain and phase shifts in the feedback loop. These values are a predetermined part of the electronics blocks in FIG. 4 and are set in accordance with standard engineering practice. In addition, many of the materials that might be used for the electro-optic substrate will only yield a positive change in refractive index with applied voltages. For these materials a common bias voltage can be applied to the first and second offset inputs to set the refractive index at some pre-biased condition. Positive and negative changes in refractive index can then be obtained.

Unlike open loop operation, closed loop operation does not produce a useful signal at the output of the divide circuit. However, the signal at range image output 86 is proportional to the change in optical path required to bring the divide circuit output to zero. Moreover, the linearity of the range image output 86 is no longer dependent on the transfer function in FIG. 2, but depends on the linearity of the electro-optic effect, which is highly linear. Thus, closed loop operation is able to track the target optical path length, increases linearity and yields a superior signal to-noise ratio over open loop operation. Detailed computer models of the system indicate that displacements as small as 0.01 nanometer are detectable.

As shown in FIG. 4, an additional feature is a feedback loop that maintains constant total intensity at the outputs 34 and 36 of the first and second detectors. For weak reflectance from the target, the signal-to-noise of the range image output 86 suffers. Since the range image output 86 is independent of the point light source intensity, the range image output 86 is increased to compensate for the weak reflectance. This process is automated through use of a second operational amplifier 76 and second bias input 84, see FIG. 4. The output of first sum circuit 66 is connected to the inverting input of the second operational amplifier 76. Second bias input 84 is connected to the non-inverting input of the second operational amplifier 76 and is set to some desired value. The output of the second operational amplifier 76 is connected to intensity control 38. As described above the second operational amplifier 76 drives its output to a value that causes the difference between the inverting and non-inverting inputs to be zero. In this scenario, an increase in the output from the first sum circuit 66 causes a decrease in the output of the second operational amplifier 76, which in turn reduces the light intensity at the first and second detectors 30 and 32, thereby reducing the output of the first sum circuit 66.

Thus, a feedback loop is formed which maintains a constant total intensity at the first and second detectors 30 and 32.

Figure 5:
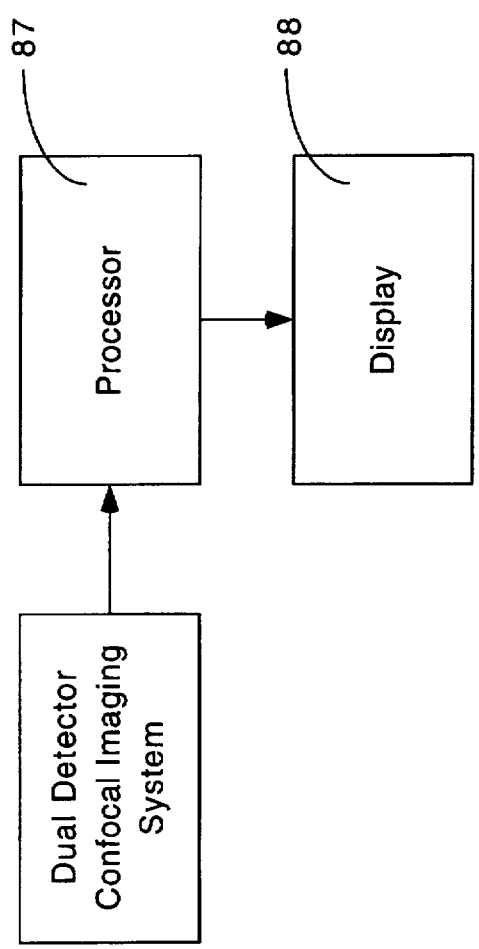
FIG. 5 is a functional block diagram of the imaging system of FIG. 4 coupled to a processor and a display device.

As shown in FIG. 5, the range image output 86 is image and display processed by processor 87 for display on display device 88. The range image output 86 may be processed in a variety of different ways to exhibit the values present in the range image output 86.

The dual detector confocal imaging system is also suited for tasks in optical interferometry, such as surface profilometry. The system provides for imaging the internal characteristics of semiconductor devices. The specific internal characteristics imaged are carrier density (or current), voltage potential, and temperature. For convenience this imaging process is referred to as IVT imagery, a device that performs the IVT imaging is an IVT imager and an image produced from the IVT imaging process is an IVT image. I is for current, V is for voltage and T is for temperature. IVT imagery can be utilized for a variety of semiconductor diagnostics, such as thermal management, detection of dead devices, detection of excessive current flow, detection of voltage breakdown points and other diagnostics obvious to those versed in the area of semiconductor diagnostics.

Figure 6:
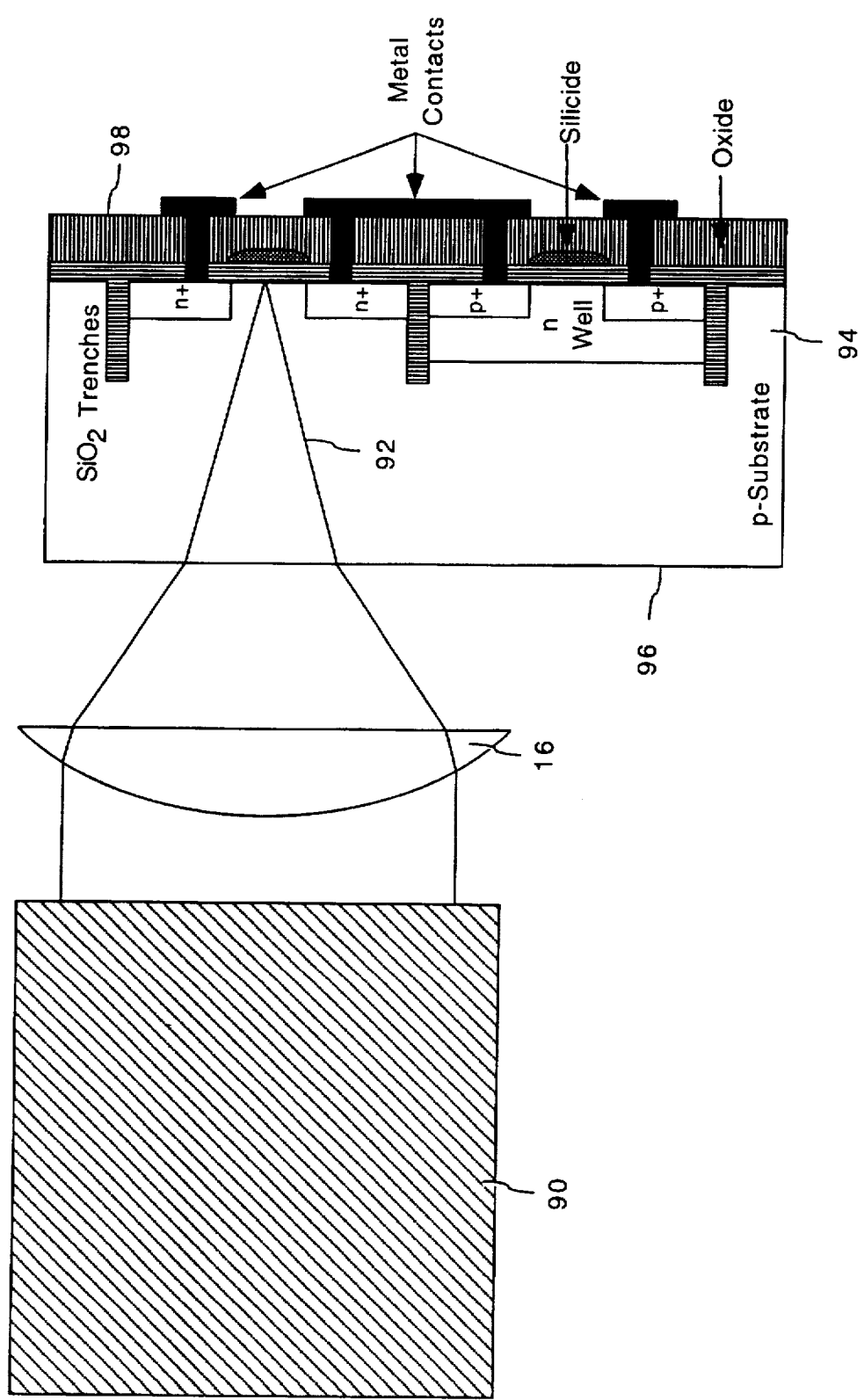
FIG. 6 is a functional diagram of the dual detector confocal imaging system of FIG. 4 used to image a semiconductor circuit.

FIG. 6 illustrates an IVT imaging process. For clarity the optical and electrical components shown in FIGS. 1, 3, and 4 are reduced to a single functional block, imaging system 90, with the exception of second lens 16. Second lens 16 is shown separately in order to emphasis the nature of the interaction between optical probe beam 92 and semiconductor device 94. The semiconductor device 94 replaces target 18 in FIG. 1. The details of semiconductor device 94 shown in FIG. 6 are typical of a COS-MOS type electronic circuit. In IVT imaging an optical wavelength is chosen which is below the semiconductor bandedge, where the semiconductor is relatively transparent. For example, the bandedge in GaAs occurs at a wavelength around 0.85 micrometers. For shorter wavelengths, above the bandedge, GaAs is highly absorptive. For longer wavelengths GaAs is transparent.

Thus, the light from a YAG laser at 1.064 micrometers will pass through GaAs with mainly reflection losses at the air-semiconductor interface due to the large (3.6) refractive index of GaAs. Other semiconductors will behave similarly, though the specific numerical values will vary.

As shown in FIG. 6, the optical beam 92 passes through the first (bottom) surface 96 of the semiconductor 94 and is focused onto the second (top) surface 98. The optical beam 92 reflects off the second surface, passes back through the semiconductor 94 to be collected by second lens 16. The collected light is then processed by imaging system 90 as described above. Reflection is from either the semiconductor metalization or from the air-semiconductor interface. In a typical semiconductor circuit, devices are only fabricated on the top surface. The bottom surface is of a semiconductor circuit is often metalized. This metalization may be replaced with a transparent electrode or holes may be placed in the metalization as needed.

As described in the background section, the carrier density, voltage potential, and temperature change the refractive index of a semiconductor. If these changes in refractive index occur at the focus of optical probe beam 92, the refractive index changes induce a change in the optical path length of the probe beam 92. The change in optical path length produces a signal in image system 90 as described above. Scanning optical probe beam 92 produces an image signal, as is typical of a confocal imaging system.

The potential difficulty with the imaging process just described is that the IVT image signals are relatively weak, representing optical path length differences of only a fraction of a micrometer. In a typical semiconductor circuit, the optical distance between the front and back surface varies significantly with the optical probe beam position, often by several micrometers. In addition the amount of light reflected from the top surface of the semiconductor can also vary by as much as an order of magnitude. This variation is referred to as reflectance variation. Imaging system 90 implicitly removes the reflectance variations. Extraction of the small IVT image signals from the large optical path length background signals is accomplished by allowing the IVT image signal to vary in time. Since the IVT image signals are a result of the actual operation of the semiconductor circuit, the requirement for time varying signals is readily obtained.

Figure 7:
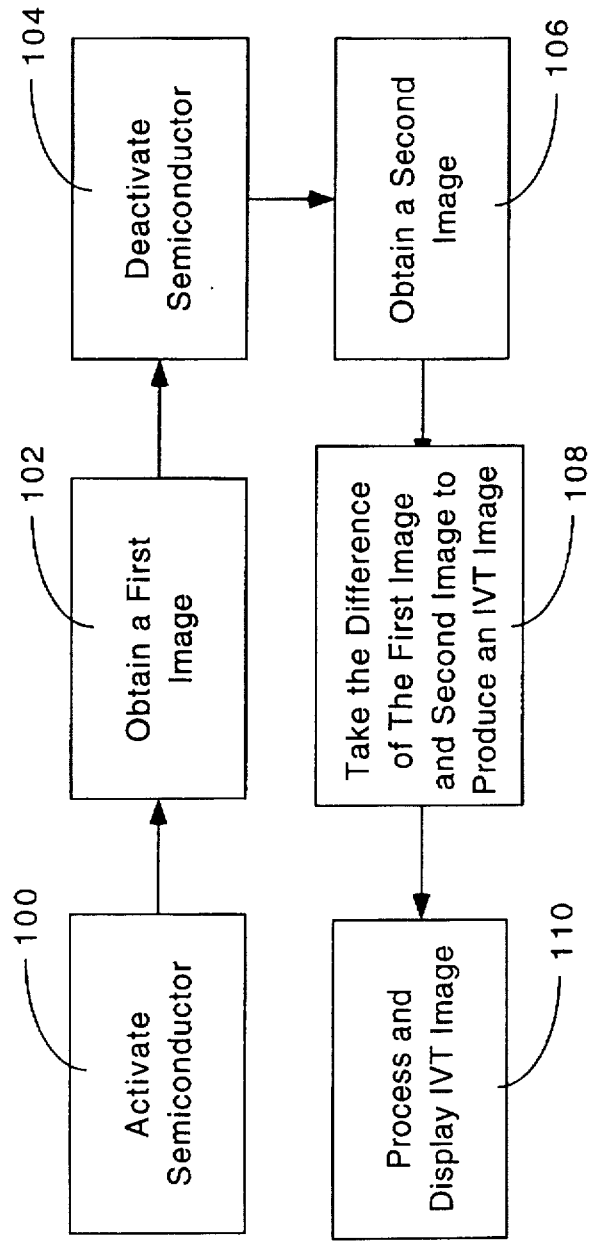
FIG. 7 is a flow diagram of a method performed by the dual detector confocal imaging system of FIG. 4 used to image a semiconductor circuit.

There are three modes of operation in which imaging system 90 can be used to obtain time varying signals. In the first mode, as shown in FIG. 7, the semiconductor device is turned on at block 100, and a first image obtained at block 102. The semiconductor device is then turned off at block 104 and a second image is obtained at block 106. The two images are then subtracted to produce an IVT image at block 108. The IVT image is processed and displayed at block 110. The IVT image is displayed in a range of intensity values. The intensity values correspond to changes in either the carrier density, voltage potential or temperature of the semiconductor circuit depending on the circuit's mode of operation. The images can be from either the open loop or closed loop configurations. Closed loop operation is required when the optical path length background exceeds the range of operation of the open loop configuration.

A second mode of operation is used when the semiconductor circuit is modulated at a fast speed as compared to the dwell time for each image pixel. In this second mode the closed loop feedback response time is set slow compared to the electronic modulation rate but fast enough to track the optical path length background. The response of the signal conditioning electronics 56 is set fast enough to sense the electronic modulation. In this case the feedback loop tracks the average value defined by the optical path length background. The time varying signal due to the semiconductor device is averaged out in the feedback electronics 59 in imaging system 90, but will be present at the output of the signal conditioning electronics 56. For periodic signals, standard frequency selective techniques (e.g. spectral analyzers and phase lock loops) can be used to increase the detection sensitivity.

A third mode of operation is needed for very high speed electronic circuits. Ones that can exceed the frequency response of the detectors and amplifiers in imaging system 90. Use of a pulsed optical beam can freeze the temporal variation in place. The detector need only measure the integrated intensity of the pulse in order to extract the desired signal. The system bandwidth is now determined by the length of the optical pulse, not the detector bandwidth. Flash photography is a well known example of this phenomenon. Repetitive sampling at different temporal points during the electronic signal will map out its temporal variation in a fashion similar to the methodology used in sampling oscilloscopes. A sequence of images produced by this technique can be played back at slow speed to produce a movie of the temporal variation.

Several other configurations of confocal imaging systems including transmission imaging can be used as the illumination component of the imaging system and the first section of the collection and detection part of the current invention. These different confocal configurations are well known to those versed in the art.

While the preferred embodiment of the invention has been illustrated and described, it will be apparent that various changes can be made therein without departing from the spirit and scope of the invention.

The embodiments of the invention in which an exclusive property or privilege is claimed are defined as follows:

1. An optical path length imaging system comprising
   a) a radiant energy point source for generating radiant energy;
   b) means for focusing the radiant energy generated by the point source onto a target and scanning the target with the focused radiant energy;

c) means for collecting the focused radiant energy that is scattered from said target;

d) means for splitting the collected radiant energy into two paths;

e) means for focusing each of the two paths of the collected radiant energy onto separate focal spots;

f) a pair of spatial filters which pass a portion of the focused radiant energy in relation to the optical path to said target, one spatial filter for each of the two paths of the collected radiant energy with one of the spatial filter being placed at one of the focal spots, wherein the spatial filters are offset from each other along the path of the focused radiant energy;

g) means for separately detecting the focused radiant energy which passed through each of the spatial filters and producing signals proportional to the quantity of detected focused radiant energy present; and h) means for generating an image signal by combining said produced signals, wherein said image signal is related to the distance traveled by the radiant energy from the focusing means to the target and back to the collecting means.

2. The imaging system in claim 1, wherein the radiant energy is optical radiation.

3. The imaging system in claim 2, wherein the focusing means comprises of a first lens for collimating the optical radiation, and a second lens for focusing the collimated optical radiation onto the target; the collecting means comprises the second lens for collimating the scattered optical radiation from the target along the optical path to the first lens, and a beam splitter for redirecting the optical radiation to the splitting means; the splitting means is a Wollastan prism, the means for focusing the optical radiation is a third lens, the spatial filters are pinholes, wherein the offset of the pinholes is mechanically set to a predetermined value, and the means for separately detecting is a pair of photodetectors; and further comprising electronic means for producing an image signal wherein said image signal is the difference in the signals generated by the pair of photodetectors divided by the sum of the signals generated by the pair of photodetectors, said image signal is produced according to the optical path length between the second lens and the target with the exact nature of the relationship being determined by the particular values of the pinhole offsets and said image signal being independent of the return optical intensity.

4. The imaging system in claim 1, further comprising means for controlling the spatial filter offsets.

5. The imaging system in claim 3, further comprising means for electronically controlling the pinhole offset.

6. The imaging system in claim 5 wherein the means for electronically controlling comprises an electro-optic substrate placed between the third lens and the pinholes, wherein said electro-optic substrate comprises a transparent electrode on one side which is common to both optical paths and a pair of transparent electrodes on the opposing side with each of the pair arranged to intersect only one of the pair of optical paths produced by the combination of the Wollastan prism and the third lens, and means for applying a voltage to at least one of the transparent electrodes and changing the optical path associated with the at least one of the transparent electrodes with the applied voltage according to the applied voltage.

7. The imaging system of claim 1, further comprising means for changing the common spatial filter offset in proportion to the path length of the radiant energy extending from the focusing means to the target then to the collecting means.

8. The imaging system of claim 6, further comprising electronic feedback for changing the common pinhole offset according to changes in the optical path length between the second lens and the target, said electronic feedback means further comprising a feedback amplifier which applies a common voltage between the pair of transparent electrodes and the common transparent electrode of the electro-optic substrate for maintaining a constant value of the image signal with the applied common voltage becoming a new image signal, thereby obtaining a closed loop system, wherein signal linearity is determined by the linearity of the electro-optic substrate and the closed loop system tracks changes in the optical path length between the second lens and the target.

9. The imaging system of claim 1, further including means for changing the intensity of the radiant energy point source in order to maintain a constant return of collected radiant energy.

10. The imaging system of claim 3, further comprising means for changing the intensity of the optical radiation point source to maintain a constant total intensity at the pair of photodetectors, said means for changing the intensity of the point source further comprising a feedback amplifier circuit, wherein said feedback amplifier circuit applies a signal to the point source for maintaining a constant value of the sum of the outputs from the photodetectors according to the sum of the optical radiation intensities measured by the photodetectors, thereby allowing maintenance of a signal-to-noise ratio in the image signal which is independent of the targets optical characteristics.

11. The imaging system of claim 1, further comprising a display device for displaying the generated image signal.

12. A method of imaging temporal changes or modulations of the path length of a radiant energy beam generated by a radiant energy source reflected off a target and to a radiant energy detector and in the amount of radiant energy returned to the detector, said method comprising the steps of:

producing a plurality of image signals of the target separated in time and proportional to said path length, wherein said target comprises spatial variations and wherein the produced plurality of image signals are independent of background spatial variations in the path length between the detector and the target, and in the amount of radiant energy returned to the detector; and generating a modulation image signal according to the produced plurality of image signals.

13. The method of claim 12, wherein the radiant energy beam is an optical radiation beam.

14. The method of claim 13, wherein the target is a semiconductor device, further comprising the steps of:

activating the semiconductor device;

producing a first plurality of image signals of the activated semiconductor device;

generating a first modulation image signal according to the produced first plurality of image signals;

deactivating the semiconductor device;

producing a second plurality of image signals of the deactivated semiconductor device;

generating a second modulation image signal according to the second plurality of image signals; and generating an IVT image by taking the difference between the first and second modulation image signals.

15. An optical path length imaging system comprising a) a radiant energy point source for generating radiant energy;

b) a first focuser for focusing the radiant energy generated by the point source onto a target and scanning the target with the focused radiant energy;

c) a collector for collecting the focused radiant energy that is scattered from said target;

d) a splitter for splitting the collected radiant energy into two paths;

e) a second focuser for focusing each of the two paths of the collected radiant energy onto separate focal spots;

f) a pair of spatial filters which pass a portion of the focused radiant energy in relation to the optical path to said target one spatial filter for each of the two paths of the collected radiant energy with one of the spatial filter being placed at one of the focal spots, wherein the spatial filters are offset from each other along the path of the focused radiant energy;

g) detectors for separately detecting the focused radiant energy which passed through each of the spatial filters and producing signals proportional to the quantity of detected focused radiant energy present; and h) a processor for generating an image signal by combining said produced signals, wherein said image signal is related to the distance traveled by the radiant energy from the focusing means to the target and back to the collecting means.

* * * * *

UNITED STATES PATENT AND TRADEMARK OFFICE
CERTIFICATE OF CORRECTION

PATENT NO. : 5,754,298
DATED : May 19, 1998
INVENTOR(S) : R.A. Falk

It is certified that error appears in the above-identified patent and that said Letters Patent is hereby corrected as shown below:

COLUMN      LINE

17              12           after "target" insert --,--
(Claim 15,  line 15)

Signed and Sealed this

Twenty-second Day of September, 1998

Attest:

BRUCE LEHMAN

Attesting Officer                Commissioner of Patents and Trademarks